United States Patent [19]

Goldberg et al.

[11] Patent Number: 5,188,828

[45] Date of Patent: Feb. 23, 1993

[54] INTERLEUKIN-6 TO STIMULATE ERYTHROPOIETIN PRODUCTION

[75] Inventors: Mark A. Goldberg; William C. Faquin, both of Boston, Mass.

[73] Assignee: Brigham and Women's Hospital, Boston, Mass.

[21] Appl. No.: 610,221

[22] Filed: Nov. 8, 1990

[51] Int. Cl.$^5$ ................... A61K 45/05; C07K 13/00
[52] U.S. Cl. ................... 424/85.2; 514/8; 514/12; 530/351
[58] Field of Search ............ 424/85.2; 530/351; 514/8

[56] References Cited

PUBLICATIONS

Miller et al. (Jun. 1990) New Engl. J. Med. 322(24):1689–1692.
Doweiko et al. (1991) Oncology 5(8):31–37.
Schuster et al. (1992) Br. J. Hematology 81:153–159.
Fried, W. (1972) Blood 40(5):671–677.
Tan et al. (1991) Kidney Int. 40:69–76.
Goldberg (1990) "Erythropoietin in Clinical Applications", Marcel Dekker, Inc., New York, pp. 59–104.
Bondurant et al. (1986) Mol. Cell. Biol. 6(7):2731–2733.
Moore et al. (1986) "Delivery Systems for Peptide Drugs", Plenum Press, N.Y., pp. 317–329.
Ishibashi et al. (Sep. 1989) Blood 74(4):1241–1244.
Gardner et al. (Jun. 1, 1990) Blood 75(11):2150–2155.
Geiger et al. (1988) Eur. J. Immunol. 18:717–721.
Takatsuki et al. (1988) J. Immunol. 141(9):3072–3077.
Bot et al. (1989) Blood 73(2):435–437.
Rennick et al. (1989) Blood 73(7):1828–1835.
Faquin et al. (1992) Blood 79(8):1987–1994.
Kitahara et al. (Oct. 1990) Jpn. J. Cancer Res. 81(10):1032–1038.
Mule et al. (Mar. 1, 1990) J. Exp. Med. 171(3):629–636.
Goldberg et al. (1988) Science 242:1412–1415.
Brakenhoff et al. (Aug. 15, 1989), J. Immunology 143(4):1175–1182.
Goldberg et al. (1987), Proc. Natl. Acad. Sci. U.S.A. 84:7972–7976.
Baumann et al. (Nov. 25, 1988) J. Biol. Chem. 263(33):17390–17396.
Ulich et al. (Jan. 1989), Blood 73(1):108–110.

*Primary Examiner*—Robert A. Wax
*Assistant Examiner*—Richard C. Ekstrom
*Attorney, Agent, or Firm*—Sterne, Kessler, Goldstein & Fox

[57] ABSTRACT

The invention is directed to the administration of Interleukin 6 for the purpose of enhancing endogenous erythropoietin levels in vitro and in vivo. The invention further encompasses methods of treatment of disorders characterized by, or including, erythropoietin deficiency. Such disorders include the anemias of chronic inflammation, renal failure, AIDS, and malignancy.

8 Claims, 2 Drawing Sheets

FIG. 2

INTERLEUKIN-6 TO STIMULATE ERYTHROPOIETIN PRODUCTION

STATEMENT AS TO RIGHTS AS TO INVENTIONS MADE UNDER FEDERALLY SPONSORED RESEARCH AND DEVELOPMENT

Part of the work leading to this invention utilized U.S. government funds. The U.S. government has certain rights in this invention.

BACKGROUND OF THE INVENTION

1. Field of the Invention

The present invention relates to the use of interleukin-6 to stimulate the production of endogenous erythropoietin in cells in vitro and in vivo. The invention further includes methods of treatment wherein interleukin-6 is administered to humans and animals having disorders which are manifested by erythropoietin deficiency. The invention also includes methods of producing erythropoietin in vitro.

2. Description of the Background Art

The Biology of Erythropoietin

Early investigations by Reissmann, using a parabiotic rat model (Reissmann, K. R., *Blood* 5:372-80 (1950)), provided strong evidence for the humoral regulation of erythropoiesis. Later studies by Erslev (Erslev, A., *Blood* 8:349-57 (1953)), provided further evidence that a hormone, an erythropoietin, was involved in the regulation of red blood cell production. Subsequent studies were undertaken attempting to purify this hormone and to understand the mechanism by which its production is physiologically regulated.

To achieve the above aims, it became important to determine the sites of erythropoietin production. In 956 and 1957, Jacobsen and his colleagues determined that the kidney is the primary site of erythropoietin production (Fried, W., et al., *Proc Soc Exo Biol Med* 2:203-7 (1956); Jacobson, L.O., et al., *Nature* 79:633-4 (1957)). Many subsequent in vivo studies and studies in isolated kidney preparations have confirmed that the kidneys are the principal site of erythropoietin production in adult mammals (Kuratowska, Z., et al., *Blood* 18:527-34 (1961); Erslev, A.J., *Am J Med* 58:25-30 (1975); Fisher, J. W., et al., *Blood* 29:114-25 (1967)). This finding is clearly illustrated by the following observations: (a) serum erythropoietin levels are lower than would be expected for the degree of anemia seen in patients with end-stage renal disease (Caro, J., et al., *J Lab Clin Med* 93:449-58 (1979)) and (b) the anemia or renal failure can be completely alleviated by the administration of recombinant human erythropoietin (Eschbach, J. W., et al., *N Enol J Med* 316:73-8 (1987); Winearls, C. G., et al., *Lancet* 2:1175-8 (1986)).

Although the investigations of Jacobsen clearly demonstrated that the kidney plays a central role in the production of erythropoietin, Nathan et al. (Nathan, D. G., et al., *J Clin Invest* 43:2158-65 (1964)) demonstrated regulation of erythropoiesis in an anephric man. In addition, Fried et al. (Fried et al., *J Lab Clin Med* 73:244-8 (1969)), demonstrated the presence of erythropoietin in the serum of nephrectomized rats. The production of erythropoietin was regulated by the degree of hypoxia to which the animals were exposed. Hence it appeared that the kidney was not the sole organ capable of producing erythropoietin. Subsequently, the role of the adult liver as an erythropoietin-producing organ, particularly in times of stress, has been confirmed by multiple investigators (Naughton, B. A., et al., *Science* 196:301-2 (1977); Caro, J., et al., *Am J Physiol* 244:E43-1-4 (1983); Beru, S., et al., *Mol Cell Biol* 7:2571-5 (1986); Bondurant, M., et al., *Mol Cell Biol* 6:2731-3 (1986)). Other Studies have shown that the liver is the primary site of erythropoietin production in the fetus (Zanjani, E. D., et al. *J Lab Clin Med* 83:281-7 (1974); Zanjani, E. D., et al., *J Lab Clin Med* 89:640-4 (1977); Zanjani, E. D., et al., *J Lab Clin Med* 67:1183-8 (1981); Flake, A. W., et al., *Blood* 70:542-5 (1987)). The switch in the primary site of erythropoietin production from the liver to the kidney occurs gradually beginning the last third of the gestational period, and is completed approximately 40 days after birth (Zanjani, E. D., et al., *J Lab Clin Med* 67:1183-8 (1981)); Flake, A. W., et al., *Blood* 70:542-5 (1987)).

Although the physiologically important erythropoietin-sensitizing organs are believed to be the kidney and the liver, there have been reports of erythropoietin production by a subpopulation of murine bone marrow macrophages (Rich, I. N., et al., *Blood* 60:1007-18 (1982); Vogt, C., et al., *Exp Hematol* 17:391-7 (1989)). Finally, various tumors have been reported to secrete erythropoietin or an erythropoiesis-stimulating activity. This production of erythropoietin has been most commonly reported to occur in renal tumors, primarily renal cell carcinomas (Kazal, L. A., et al., *Ann Clin Lab Sci* 5:98-109 (1975); Hagiwara, M., et al., *Blood* 63:828-35 (1984); Sherwood, J. B., et al., *Endocrinology* 99:504-10 (1976); Sherwood, J. B., et al., *Proc Natl Acad Sci USA* 83:165-9 (1986)) and hepatomas (Davidson, C. S., *Semin Hematol* 13:115-9 (1976)); however, it has also been associated with uterine fibromyomas (Naets, J. P., et al., *Scand J Haematol* 19:75-8 (1977)), cerebellar hemangioblastomas (Waldmann, T. A., et al., *Ann NY Acad Sci* 149:509-15 (1968)), aldosterone secreting adrenal adenomas (Mann, D. L., et al., *Ann Int Med* 66:335-40 (1967)), and pheochromocytomas (Bradley, J. E., et al., *J Urol* 86:1-6 (1961)).

Regulation of Erythropoietin Production in a Cell Line

Both the HepG2 and Hep3B cell lines produce large amounts of biologically active and immunologically identifiable erythropoietin in response to hypoxia or cobalt chloride. RNA blot analysis has demonstrated that the production of erythropoietin in these cells is regulated at the level of mRNA. These two cell lines were generated from human hepatic carcinomas (Aden, D. P., et al., *Nature* 282:615-6 (1979)); they have been shown histologically and biochemically to possess characteristics of well-differentiated liver parenchymal cells (Aden, D. P., et al., *Nature* 282:615-6 (1979); KnoWles, B. B., et al., *Science* 209:497-9 (1980)). Both have many of the biosynthetic capabilities of normal hepatocytes, and they have been shown to secrete 17 of the major plasma proteins into cell culture medium, including albumin and alphafetoprotein. Further evidence suggesting that this cell line accurately reflects the normal physiological situation in vivo is provided by RNA blot hybridization analysis. The erythropoietin mRNA size is indistinguishable from that previously reported for RNA from normal human fetal liver (Jacobs, K., et al., *Nature* 313:806-10 (1985)). In addition, the finding that regulation occurs at the mRNA level is in agreement with previous in vivo data (Beru, S., et al., *Mol Cell Bio*

7:2571-5 (1986); Bondurant, M., et al., *Mol Cell Bio* 6:2731-3 (1986)).

RNA blot analyses from hypoxic and nonhypoxic kidney tissue have shown that erythropoietin synthesis in the mouse kidney is regulated at the level of RNA (Beru, S., et al., *Mol Cell Bio* 7:2571-5 (1986); Bondurant, M., et al., *Mol Cell Bio* 6:2731-3 (1986)). Erythropoietin synthesis in the human hepatoma cell line, Hep3B, is also regulated at the RNA level with a greater than 100-fold increase in erythropietin mRNA levels after the cells have been made hypoxic or exposed to cobalt chloride for 24 hours (Goldberg, M. A., et al., *Science* 242:1412-5 (1988)). Furthermore, protein synthesis was necessary prior to hypoxia or cobalt-induced increase in erythropoietin mRNA in the Hep3B cells. Similar findings have been reported in hypoxic mouse kidneys (Schuster, S. F., et al., *Blood* 70:316-8 (1987)). Recently, Goldberg et al. (Goldberg, M. A., et al., *Blood* 74:716A ()1989)) have found only a five- to ten-fold increase in the rate of erythropoietin gene transcription in Hep3B cells exposed to hypoxia or cobalt and have presented data suggesting a significant post-transcriptional component to the regulation of erythropoietin mRNA levels as well.

Vivo Regulation of Erythropoietin Production

The maintenance of an adequate supply of oxygen to the body tissues is vital to survival. Since to a large degree the oxygen-carrying capacity of blood is governed by the concentration of erythrocytes in the blood, the appropriate regulation of erythropoiesis is also crucial. The early studies of Reissmann (Reissmann, K. R., *Blood* 5:372-80 (1950)) and Erslev (Erslev, A., *Blood* 8:349-57 (1953)) clearly demonstrated the hypoxia-induced stimulation of erythropoietin secretion. There are no preformed stores of erythropoietin in either the liver or the kidney, and hence hypoxia results in de novo production of erythropoietin (Jelkmann, W., *Pflügers Arch* 393:88-91 (1982); Schooley, J. C., et al., *Blood* 40:662-70 (1972)). Fried et al. (Fried, W., et al., *Proc Soc Exp Biol Med* 92:203-7 (1956)) noted that erythropoietin production was regulated by the relationship between oxygen supply and demand. An important point from these studies is that erythropoietin production appears to be regulated by the tissue oxygen tension at the site of the erythropoietin oxygen sensor in the kidney and liver. (Reissmann, K. R., *Blood* 5:372-80 (1950); Erslev, A., *Blood* 8:349-57 (1953); Fried, W., et al., *Proc Soc Exp Biol Med* 92:203-7 (1956); Jelkmann, W., *Pflügers Arch* 393:88-91 (1982); Schooley, J. C., et al., *Blood* 40:662-70 (1972)).

Erythropoietin Mechanism of Action: Target Cells

Unlike several of the other hematopoietic growth factors, erythropoietin is a lineage-specific hematopoietin, only influencing the growth of cells of the erythroid lineage. When erythropoietin is secreted from the erythropoietin-producing cells in response to hypoxia, it travels through the blood to its target organ, the hematopoietic tissues; in man, before birth, the principal hematopoietic tissue is within the liver, while after birth it is in the bone marrow. There, erythropoietin binds specifically to its receptor on the erythroid progenitor cells called burst forming unit-erythroid (BFU-E) and colony-forming unit-erythroid (CFU-E) and stimulates these cells to proliferate and differentiate (Spivak, J. L., *Int J Cell Cloning* 4:139-66 (1986)). BFU-E are the earliest erythroid progenitors and constitute 0.01%, approximately, of the nucleated bone marrow cells. CFU-E, which are derived from BFU-E, and account for about 0.1% of marrow cells, are much more responsive to erythropoietin (Spivak, J. L., *Int J Cell Cloning* 4:139-66 (1986); Sawada, K., et al., *J Clin Invest* 80:357-66 (1987)).

Recent studies (Koury, M. J., et al., *J Cell Physiol* 121:526-32 (1984)) have described the population of cells obtained from the spleens of mice during the acute disease caused by infection with the anemia-inducing strain of the Friend murine leukemia virus. In an elegant series of investigations, it was demonstrated that these relatively immature erythroid cells require erythropoietin in order to maintain their viability and to differentiate into mature erythrocytes (Koury, M. J., et al., *J Cell Physiol* 121:526-32 (1984); Koury, M. J., et al., *Proc Natl Acad Sci USA* 79:635-9 (1982); Koury, M. J., et al., *J Cell Physiol* 126:259-65 (1986); Bondurant, M. C., et al., *Mol Cell Biol* 5:675-80 (1985); Sawyer, S. T., et al., *J Biol Chem* 261:9187-95 (1986); Koury, M. J., et al., *J Cell Physiol* 137:65-74 (1988); Koury, M. J., et al., *Blood Cells* 13:217-26 (1987); Koury, M. J., et al., *J Cell Physiol* 133:438-48 (1987)). During differentiation in response to erythropoietin, these cells increase globin gene transcription and synthesis of hemoglobin, transfer and receptor synthesis, and the synthesis of integral erythrocyte membrane proteins. They also undergo other normal differentiation-associated events such as enucleation and extensive membrane rearrangement.

Erythropoietin Levels in Health and Disease

The low levels of erythropoietin that are always present appear to be sufficient to allow for a basal rate of erythropoiesis. Relatively small losses of blood do not appear to stimulate increased erythropoietin production (Kickler, T. S., et al., *J Am Med Assoc* 260:65-7 (1988)). It is only after a major blood loss that there is an increased production of erythropoietin and rate of erythropoiesis.

It has been well-established that the majority of patients with renal insufficiency and anemia have serum erythropoietin levels well below what would be expected for the degree of anemia (Caro, J., et al., *J Lab Clin Med* 93:449-58 (1979); Radtke, H. W., et al., *Blood* 54:877-84 (1979); Chandra, M., et al., *J Pediatr* 113:1015-21 (1988)), although they can still respond to hypoxia with an increase in serum erythropoietin levels (Radtke, H. W., et al., *Blood* 54:877-84 (1979); Chandra, M., et al., *J Pediatr* 113:1015-21 (1988)). However, this markedly blunted erythropoietin response substantially contributes to the pathogenesis of the anemia (Eschbach, J. W., et al., *Am J Kid Dis* 11:203-9 (1988)).

With the current availability of accurate immunoassays, investigators have begun to survey anemias of diverse etiologies to determine if the erythropoietin response is appropriate. There is a wide range of normal erythropoietin responses to anemia and different types of anemia may elicit different yet adequate degrees of erythropoietin response. Erslev et al. (Erslev, A. J., et al., *J Lab Clin Med* 109:429-33 (1987)) and Birgegard et al. (Birgegard, G., et al., *Br J Haematol* 65:479-83 (1987)) found that the erythropoietin response in anemic patients with rheumatoid arthritis and other inflammatory arthridities appear to be similar to the response in other types of anemias without active inflammation. On the other hand, the study by Baer et al. *(Br J Haematol* 66:559-64 (1987)) suggests that the erythropoietin response in patients with rheumatoid arthritis and anemia is blunted compared to a control population of anemias of other idiologies (including iron deficiency, malignancy, sickle cell anemia, pure red cell aplasia, aplastic anemia, pernicious anemia, sideroblastic anemia secondary to alcoholism, and other chronic, inflammatory disorders. Hochberg, MC, et al. *(Arthritis and Rheumatism* 31:1318-21 (1988)) also reported that patients with rheumatoid arthritis have an impaired serum immunoreactive erythropoietin response to anemia compared to a control group with iron deficiency anemia. Similarly, there are reports of blunted erythropoietin responses for a given degree of anemia in patients with cancer (Miller, C. B., et al., *Proc Am Soc Clin Oncol* 8:182 (1989)), AIDS (Spivak, J. L., et al. *J Am Med Assoc* 261:3104-7 (1989)), thalassemia (Manor, D., et al., *Scand J Haematol* 37:221-8 (1986)), sickle cell anemia (Sherwood, J. B., et al., *Blood* 67:46-9 (1986)), and the anemia of prematurity (Brown, M. S., et al., *J Pediatr* 105:793-8 (1984)), as well as in patients who have received cis-platinum-containing chemotherapy (Smith, D. H., et al., *Proc Am Assoc Canc Res* 29:52 (1988)) and in those who have received intensive radiotherapy and/or chemotherapy while undergoing bone marrow transplantation (Schapira, L., et al., *Blood* 74:910a (1989)). Furthermore, although most patients with myelodysplastic syndromes and anemia have very high serum erythropoietin levels, there are occasional patients with unexplained extremely low levels for the degree of anemia (Jacobs A. et al., *Brit J. Haematol.* 73:36 (1989)).

In the case of sickle cell anemia, erythropoietin deserves special mention. Sherwood et al. (Sherwood, J. B., et al., *Blood* 67:46-49 (1986)) suggest that sickle cell anemia patients have low erythropoietin levels for their degree of anemia, although clearly these patients have a markedly increased rate of erythropoiesis and generally maintain reticulocyte counts in the range of 10-20%.

The Biology of Interleukin-6

The function of most cytokines that are known to be involved in the regulation of the immune response and hematopoiesis is not limited to a specific lineage of cells. These cytokines display a variety of biological functions on various tissues and cells. Interleukin-6 is a typical example of a multifunctional cytokine. The fact that this cytokine regulates immune responses, hematopoiesis, and acute phase reactions, indicates that it has a major role in host defense mechanisms.

Originally, human interleukin-6 was identified as B cell growth factor-2 or BSF2. It was found in the culture supernatants of mitogen- or antigen-stimulated peripheral mononuclear cells and shown to induce immunoglobulin production in B cell lines (Muraguchi, A., et al., *J Immunol* 127:412 (1981)). This factor was distinguishable from other factors, such as interleukin-2, 4, and 5 (other factors that affect B cells). BSF2 was purified to homogeneity from the culture supernatant of a human T cell leukemia virus type-1 (HTLV-1) transformed T cell line and its partial N-terminal amino acid sequence was determined (Hirano, T., et al., *Proc Natl Acad Sci USA* 82:5490 (1985)).

Around the time of the studies of BSF2, the nucleotide sequences of the molecules designated as interferon beta-2 (IFN$\beta_2$) (Zilberstein, A., et al., EMBO 5:2529 (1986)) and 26 Kd protein were reported (Haegeman, G., et al., *Eur J Biochem* 159:625 (1986)). The sequencing studies revealed that BSF2, IFN$\beta_2$, and 26 Kd protein were identical proteins. Subsequently, recombinant interleukin-6 was shown to lack any interferon activity and to have no antigenic or functional relation to IFN$\beta$ (Hirano, T., et al., *Immunol Lett* 17:41 (1988)).

In addition to the function of interleukin-6 in the immune response, the cytokine functions in the induction of acute phase proteins in hepatocytes where it induces the production of major acute phase proteins (Gauldie, J., et al., *Proc Natl Acad Sci USA* 84:7251(1987); Andus, T., et al., *FEBS Lett* 221:18 (1987)). Table 1 summarizes the molecules identified to be identical to interleukin-6.

TABLE 1

| Molecules Identical to Interleukin-6 |
|---|
| 1. B cell stimulatory factor 2 |
| 2. Interferon beta 2 |
| 3. 26 Kd protein |
| 4. Myeloma/plasmacytoma growth factor |
| 5. Hepatocyte stimulating factor |
| 6. Macrophage granulocyte inducing factor 2 |
| 7. Cytotoxic T cell differentiation factor |

Immune system: Originally, interleukin-6 was found to be produced by T cells and shown to play a role in the induction of the late maturation of B cells into antibody-producing cells (Muraguchi, A., et al., *J Immunol* 127:412 (1981); Hirano, T., et al., *Proc Natl Acad Sci USA* 82:5490 (1985)). Interleukin-6 was also effective in in vivo antibody production in mice (Takatsuki, F., et al., *J Immunol* 141:3072 (1988)). A study with anti-interleukin-6 antibody demonstrated that interleukin-6 is one of the essential factors for antibody production in B cells (Muraguchi, A., et al., *J Exo Med* 167:332 (1988)).

The effect of interleukin-6 is not restricted to B cells, however. It can also act on T cells. Activated but not resting B cells express interleukin-6 receptors while resting T cells express interleukin-6 receptors (Taga T., et al., *J Exp Med* 166:967 (1987)). This result indicates that interleukin-6 acts only on the final maturation stage of activated B cells and is effective on resting T cells. In the presence of interleukin-2, interleukin-6 was also shown to induce differentiation of cytotoxic T cells (CTL) from murine and human thymocytes and spleen. (Takai, Y., et al., *J Immunol* 140:508 (1988); Okada, M., et al., *J Immunol* 141:1543 (1988)).

Acute phase Reactions: The acute phase response is a systemic reaction to inflammation or tissue injury that is characterized by leukocytosis, fever, increased vascular permeability, alterations in plasma metal and steroid concentrations, and increased levels of acute phase proteins. Several acute phase proteins are induced by interleukin-6, such as fibrinogen, alpha-1-antichymotrypsin, alpha-1-acid glycoprotein, and haptoglobin in human hepatoma cell line, HepG2. Serum amyloid A, C-reactive protein, and alpha-1-antitrypsin in human primary hepatocytes are also induced by interleukin-6 (Castell, J. V., et al., *FEBS Lett* 232:347 (1988)). In vivo administration of interleukin-6 in rats also induced characteristic acute phase reactions. The results confirmed the in vivo role of interleukin-6 in acute phase reaction (Geiger, T., et al., *Eur J Immunol* 18:717 (1988)).

Interleukin-6 Signals: Interleukin-6 provides multiple signals on various tissues and cells. These signals can be divided into three categories: (a) induction of differentiation or specific gene expression such as immunoglobulin induction in B cells, induction of acute phase proteins in hepatocytes, induction of cytotoxic T cell differentiation, induction of neural cell (PC12) differentiation, and activation of hematopoetic stem cells from $G_0$ to $G_1$; (b) stimulation of cell growth, such as the induction of myeloma/plasmocytoma growth or T cell growth, and induction of mysangial cell growth; (c) inhibition of cell growth such as inhibition of growth of myeloid leukemia cells or breast cancer cells.

Hematopoiesis: The effect of interleukin-6 on hematopoiesis was first described by Ikebuchi et al. (Ikebuchi, K., et al., *Proc Natl Acad Sci USA* 84:9035 (1987)). It was found that interleukin-3 and interleukin-6 act synergistically in the formation of multi-lineage blast cell colonies in murine spleen cell cultures. The appearance of these cell colonies induced by IL-3 was significantly hastened by the addition of interleukin-6, suggesting that interleukin-6 activates hematopoetic stem cells at the $G_0$ stage to enter into the $G_1$ phase.

Human and murine myeloid leukemia cell lines such as human histiocytic U937 cells and mouse myeloid M1 cells can be induced to differentiate into macrophages and granulocytes in vitro by several synthetic and natural products. Recently, interleukin-6 was also shown to induce differentiation of M1 cells into macrophages (Miyaura, C., et al., *FEBS Lett* 234:17 (1988)).

Recent studies by a number of different laboratories have demonstrated that interleukin-6 affects the growth and/or differentiation of a diversity of hematopoietic cell types. In vitro studies assessing the effect of interleukin-6 on bone marrow progenitor cells from adult bone marrow and fetal cord blood demonstrated that interleukin-6 induced cycling and clonogenic maturation of CFU-Mix, CFU-GM, and BFU-E (Gardner et al., *Blood* 75:2150–2155 (1989)). Other in vitro studies in which growth of hematopoietic precursors was measured, showed that combinations of interleukin-6 and either M-CSF, GMCSF, G-CSF, IL-3, or IL-4 enhanced the total number and/or colony size of erythroid, myeloid, megakaryocytic, and multilineage colonies (Bot, et al., *Blood* 73:435–437 (1989); Rennick, D. et al., *Blood* 73:1828–1835 (1989)).

Interleukin-6 has also been shown to affect the growth or proliferation of a diversity of hematopoietic cell types in vivo. Ishibashi et al. administered interleukin-6 parenterally to mice and measured platelet counts at various intervals. The results showed that size but not numbers of megakaryocytes was increased and that platelet counts were elevated. No change in myelopoiesis or erythropoiesis was observed. (Ishibashi,T., et al., *Blood* 74:1241–1244 (1989)). In contrast, other in vivo studies indicated that the administration of interleukin-6 to rats induced myeloid and erythroid hyperplasia (Ulich,T., et al. *Blood* 73:108–110 (1989); Ulich, T., *Am J Path* 135:663–670 (1989)).

Neither the in vitro nor the in vivo investigations addressed the mechanism(s) by which interleukin-6 exerts its effects on hematopoiesis. It was not known, until the discovery of the present invention, how interleukin-6 was able to affect erythropoiesis in vivo or in vitro.

SUMMARY OF THE INVENTION

The present invention is based on the inventors' unexpected discovery that interleukin-6 can produce a dramatic increase in the production of endogenous erythropoietin in living cells.

Accordingly, the present invention includes methods for increasing the levels of endogenous erythropoietin in cells in vitro and in vivo by the administration of interleukin-6. The invention is especially directed to methods of enhancing endogenous levels in vivo.

The present invention, thus include a method of treatment of diseases in which there is a deficiency of erythropoietin, such as the anemias of chronic inflammation, renal failure, AIDs, and malignancy, which method comprises the administration of interleukin-6.

The exemplified methods encompass the enhancement of endogenous erythropoietin levels by living cells in vitro by the administration of interleukin-6 to the cells. In a specific disclosed embodiment, incubation of hypoxic Hep3B human hepatoma cells with interleukin-6 results in a nearly 100% increase in endogenous levels of erythropoietin.

BRIEF DESCRIPTION OF THE FIGURES

FIG. 2. Effect of interleukin-6 on Hypoxia-induced erythropoietin mRNA Levels in Human Hepatoma Cells. Total RNA was extracted from Hep3B cells incubated with or without interleukin-6 in the presence or hypoxia.

DESCRIPTION OF THE PREFERRED EMBODIMENTS

Figure 1:
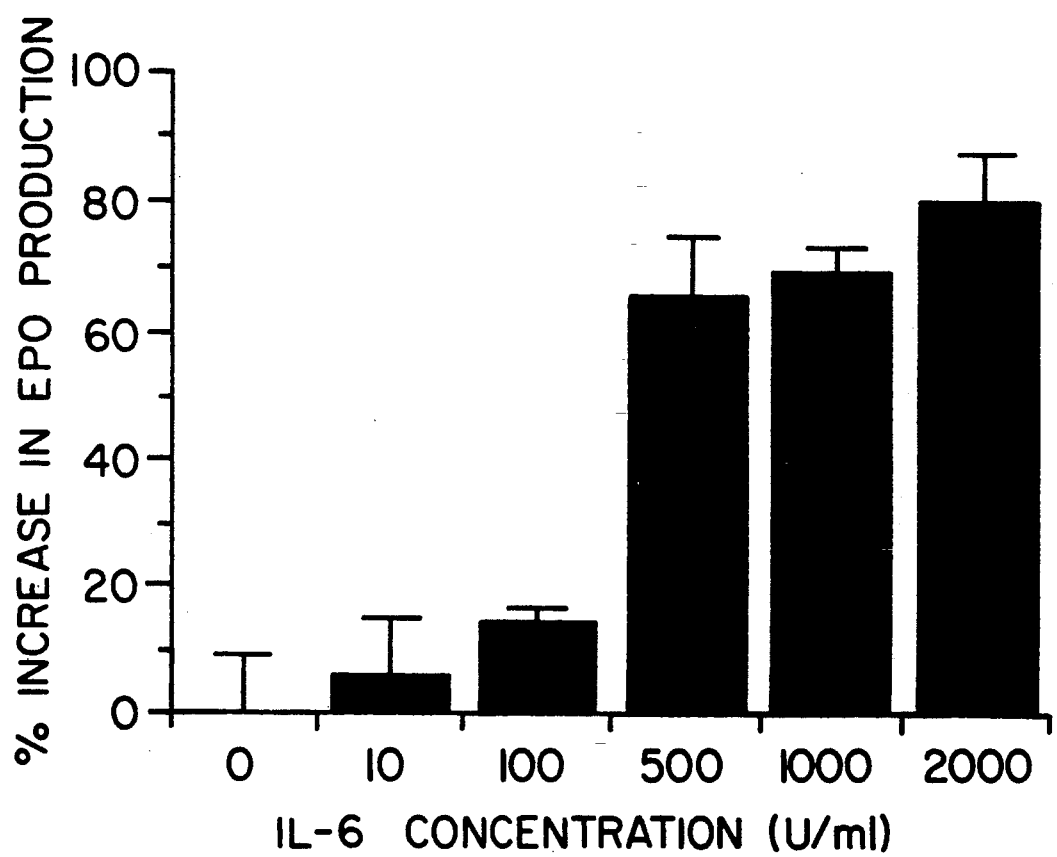
FIG. 1. Interleukin Dose-Response Curve in Human Hepatoma Cells. The human hepatoma cell line, Hep3B, which is able to produce biologically active erythropoietin in response tp hypoxia, was used to study the effects of interleukin-6 on erythropoietin production.

The present invention relates to the use of interleukin-6 to stimulate the production of endogenous erythropoietin in cells in vitro and in vivo. The invention further includes methods of treatment wherein interleukin-6 is administered to humans and animals having disorders which are manifested by erythropoietin deficiency. The invention also includes methods of enhancing erythropoietin levels in vitro.

In a preferred embodiment, interleukin-6 is administered to humans or veterinary animals in vivo. A preferred in vivo application encompasses the administration of interleukin-6 to humans having disorders that include a deficiency of erythropoietin. Such disorders generally include, but are not limited to, the anemias that accompany renal failure, AIDs, malignancy, and chronic inflammation. Other disorders include anemias not associated with the above conditions such as thalassemia, sickle cell anemia, the anemia of prematurity, anemia that accompanies cis-platinum chemotherapy, and anemia following intensive radiotherapy and/or chemotherapy plus bone marrow transplantation.

In an alternative preferred embodiment of the invention, interleukin-6 is administered to a human hepatoma cell line maintained under hypoxic conditions. Other preferred embodiments of the invention include the administration of interleukin-6 derivatives or modifications. Such derivatives or modifications retain the desirable erythropoietin-stimulating activity but may not include amino acid deletions, insertions, substitutions, or modifications.

By the terms "modifications or derivatives," for the purpose of the present invention, is intended any protein or peptide fragment that is functionally-similar to interleukin-6 in that it possesses the activity that enhances the production of erythropoietin and is derivable from the naturally-occurring interleukin-6 molecule. An interleukin-6 peptide derivative or modification is derivable from the naturally-occurring amino acid sequence of interleukin-6 if it can be obtained by fragmenting the naturally-occurring chosen sequence of interleukin-6, or if it can be synthesized based upon a knowledge of the sequence of the naturally-occurring amino acid sequence or of the genetic material (DNA or RNA) which encodes the substance.

By the term "retain", for the purpose of the present invention, is intended, retention, in an interleukin-6 modification or derivative, of erythropoietin-stimulating activity sufficient for the beneficial treatment of a given disorder in which an erythropoietin deficiency is manifested.

By the term "treating" is intended the administration to subjects of the compositions of the invention for purposes which include prophylaxis, amelioration, or cure of disease.

By the term "administer" is intended any method for introducing the compositions of the present invention into a subject. Typical methods include, but are not limited to, oral, intranasal, parenteral (intravenous, intramuscular, or subcutaneous), or rectal. When administration is for the purpose of treatment, administration may be for either a "prophylactic" or "therapeutic" purpose. When provided prophylactically, the substance is provided in advance of any symptom. The prophylactic administration of the substance serves to prevent or attenuate any subsequent symptom. When provided therapeutically, the substance is provided at (or shortly after) the onset of a symptom. The therapeutic administration of the substance serves to attenuate any actual symptom.

By the term "animal" is intended any living creature that contains cells in which erythropoietin production is stimulated in response to interleukin-6 administration. Foremost among such animals are humans; however, the invention is not intended to be so-limiting, it being within the contemplation of the present invention to apply the compositions of the invention to any and all animals which may experience the benefits of the application.

By "enhance" is intended, for the purposes of this invention, an increase in erythropoietin levels to levels greater than those levels that are present before treatment or that result from hypoxia alone.

By the term "disorder" is intended any deviation from or interruption of the normal structure or function of any part, organ, or system (or combination thereof) of the body that is manifested by a characteristic set of symptoms and signs.

By the term "hypoxic" is meant a state characterized by a reduction of oxygen supply below physiological levels. In vivo this state occurs despite the presence of an adequate blood perfusion to the tissues.

EXAMPLES

Example 1

The human hepatoma cell line, Hep3B, which is able to produce biologically active erythropoietin (erythropoietin) in response to hypoxia (Goldberg et al., *Proc. Natl. Acad. Sci. USA* 84:7972 (1987)) was used to study the effects of Il-6 on erythropoietin production. Hep3B cells were grown to confluency in 100 mm tissue culture dishes (Corning) containing 10 ml of alpha minimal essential medium (Gibco) supplemented with penicillin (100 U/ml), Streptomycin (100 ug/ml), and 10% defined supplemented calf serum (Hyclone). Cells were then incubated under hypoxic conditions (1% oxygen) for 24 hours in triplicate in 5 ml of medium with varying concentrations of Il-6. At the conclusion of the experiment, the culture medium was collected and assayed in duplicate by radioimmunoassay for erythropoietin as described previously (Goldberg et al., *Proc. Natl. Acad. Sci. USA* 84:7972 (1987)). Values shown represent the mean percent increase in erythropoietin production above that produced by hypoxia alone ± standard deviations. Il-6 was found to cause a dose-dependent increase in the production of erythropoietin in Hep3B cells by as much as 81% at a concentration of 2000 U/ml.

EXAMPLE 2

Effect of Il-6 on hypoxia-induced erythropoietin mRNA levels. Hep3B cells were grown to confluency in 150 mm culture dishes (Falcon) containing 30 ml of alpha minimal essential medium. Cells were then incubated in 20 ml medium either hypoxically (1% oxygen) or nonhypoxically (21% oxygen) for 24 hours in the presence or absence of Il-6 (1000 U/ml), Il-alpha (20 U/ml) or TNF (1000 U/ml). Total cellular RNA was isolated and an RNA blot analysis was performed as described previously (Goldberg et al., *Proc. Natl. Acad. Sci. USA* 84:7972 (1987)). Total cellular RNA (20 ug) was loaded in each lane, and the results obtained when the RNA-containing filter was hybridized with 32P-labeled erythropoietin cDNA are shown. As a control, the hybridization to radiolabeled mouse betaactin is presented at the bottom. In addition, the amount of erythropoietin produced by the cells was determined in duplicate by radioimmunoassay of the culture medium. Using densitometry to scan the blot, it was found that the steady state erythropoietin mRNA levels in the presence of Il-6 were increased 39% above the levels found with hypoxia alone. This indicates that the effect of Il-6 in increasing erythropoietin may occur at the mRNA level; however, the fact that Il-6 caused a 58% increase in total erythropoietin produced by these cells suggests that Il-6 may also have effects at other levels of gene regulation.

Having now generally described this invention, it will become readily apparent to those skilled in the art that many changes and modifications can be made thereto without affecting the spirit or scope thereof.

What is new and claimed and intended to be covered by Letters Patent of the United States is:

1. A method of enchancing erythropoietin production wherein said enhancing is effected by the administration of interleukin-6 under hypoxic conditions.

2. The method of claim 1 wherein said interleukin-6 is administered in vitro.

3. The method of claim 1 wherein said administration is in vivo.

4. A method of treating anemia in a animal wherein said treating is by the administration of interleukin-6 to said animal under hypoxic conditions.

5. The method of claim 4 wherein said anemia is present in a disorder selected from the group consisting of chronic inflammation, renal failure, and cancer.

6. The method of claim 4 wherein said administration is selected from the group consisting of oral, parenteral, nasal, and rectal administration.

7. The method of claim 6 wherein said administration is parenteral.

8. A method of enhancing the production, in cells of erythropoietin, which method comprises:
   administering interleukin-6 to said cells under hypoxic conditions.

* * * * *